United States Patent
Chang et al.

(10) Patent No.: US 6,897,185 B1
(45) Date of Patent: May 24, 2005

(54) FORMULATION FOR COUNTERACTING AND ETHYLENE RESPONSE IN PLANTS, PREPARATION PROCESS THEREOF, AND METHOD USING THE SAME

(75) Inventors: William T. H. Chang, Taipei (TW); Ren-Der Yang, Shrewsbury, MA (US)

(73) Assignee: Lytone Enterprise, Inc., Taipei (TW)

( * ) Notice: Subject to any disclaimer, the term of this patent is extended or adjusted under 35 U.S.C. 154(b) by 223 days.

(21) Appl. No.: 10/182,403

(22) PCT Filed: Sep. 22, 2000

(86) PCT No.: PCT/US00/25979

§ 371 (c)(1),
(2), (4) Date: Jul. 30, 2002

(87) PCT Pub. No.: WO02/24171

PCT Pub. Date: Mar. 28, 2002

(51) Int. Cl.⁷ .......................... A01N 25/08; A01N 27/00
(52) U.S. Cl. ....................................... 504/357; 504/360
(58) Field of Search ............................... 504/357, 360, 504/359, 326

(56) References Cited

U.S. PATENT DOCUMENTS

| 5,100,462 A | | 3/1992 | Sisler et al. |
| 5,518,988 A | | 5/1996 | Sisler et al. |
| 5,935,906 A | * | 8/1999 | Callan et al. ............... 504/130 |
| 6,017,849 A | | 1/2000 | Daly et al. |
| 6,365,549 B2 | * | 4/2002 | Sisler ......................... 504/114 |

FOREIGN PATENT DOCUMENTS

EP 0 565 354 * 10/1993

* cited by examiner

*Primary Examiner*—S. Mark Clardy
(74) *Attorney, Agent, or Firm*—Burns, Doane, Swecker & Mathis, L.L.P.

(57) ABSTRACT

Disclosed is a tablet dosage for inhibiting ethylene response in a plant containing a blocking agent, which has ethylene binding site inhibition activity to plants, and an effervescent ingredient in admixture with one or more acceptable excipients. A process of preparing the tablet dosage and a method for inhibiting ethylene response in plants are also disclosed therein.

15 Claims, No Drawings

FORMULATION FOR COUNTERACTING AND ETHYLENE RESPONSE IN PLANTS, PREPARATION PROCESS THEREOF, AND METHOD USING THE SAME

FIELD OF THE INVENTION

The invention relates to a novel tablet dosage formulation for regulating plant physiology, in particular counteracting ethylene response, containing a blocking agent and an effervescent ingredient in admixture with one or more acceptable excipients, a process for producing the same, and a method of inhibiting various ethylene responses by applying the formulation of the present invention.

BACKGROUND OF THE INVENTION

Plant hormones play important roles in plant growth responses. Ethylene is a plant growth hormone, which affects many important aspects of plant growth, development, and senescence. The most important effects of ethylene include processes associated with the ripening of fruits, the senescence of flowers, and the abscission of leaves. The commercial value of fresh produce is usually reduced by the excessive amount of ethylene gas which hastens the ripening of fruits, the senescence of flowers, and the early abscission of leaves.

Because of ethylene-induced problems, intensive research has been focused on ways to prevent or reduced its effects on plants. One of the most effective ways of mitigating the effects of ethylene employs the principle of blocking the receptor in plants that receives signals from ethylene. One of the best-known compounds for such a purpose is silver thiosulfate ("STS"). STS provides an irreversible blocking of the ethylene binding sites in plant cells and thereby prevents or reduces the harmful effects of ethylene on plants. While STS is highly effective, it poses a serious waste disposal problem since silver is a heavy metal that is toxic to most living organisms.

Sisler et al., Plant Growth Reg. 9, 1587–164, 1990 discloses that cyclopentadiene is an effective blocking agent for an ethylene binding site. An effective diazocyclopentadiene is also disclosed in U.S. Pat. No. 5,100,462. However, the cyclopentadiene and diazocyclopentadiene are unstable and have a strong odor.

U.S. Pat. No. 5,518,988 discloses the use of gaseous cyclopropene and derivatives thereof such as methylcyclopropene, as ethylene binding site blocking agents. Methylcyclopropene is effective at a very low dosage, in the parts per billion range, and is safe to be used in fruits and vegetables, as well as flowers. Methylcyclopropene is readily undergoing oxidation and other reactions so that it is highly unstable. Most recently, U.S. Pat. No. 6,017,849 encapsulates methylcyclopropene gas by a carrier. The carrier such as alpha-cyclodextrin serves to stabilize the reactivity and instability of cyclopropene gas, thereby providing a convenient and safe means of storing, transporting and applying or delivering the gas to plants.

Commercial methylcyclopropene powder products usually contain 0.43% of a methylcyclopropene gas ingredient. The gas will be released after mixing the powder with water or a buffer solution. An application rate of 0.5 g of powder per one cubic meter of the sealed space results in a final methylcyclopropene concentration of 900 parts per billion. The shelf life of flowers, fruits and vegetables can be significantly ended if they are exposed at this concentration for at least 4 hours as a post-harvest treatment.

The powder products are much more convenient to use than the products in a gas form, but are by no means user-friendly. It still has the disadvantages related to powder handling in the field, e.g. susceptibility to premature wetting and errors in measurement. Furthermore, manual mixing is normally recommended when a large quantity of powder, such as amounts more than 10 g per batch, is required for fumigating a large space. The amount of methylcyclopropene in the enclosed space may be reduced from its originally intended level due to personal entering and leaving of the enclosed space during the mixing procedure, and thus the beneficial effect of methylcyclopropene is reduced.

The present invention provides an effervescent tablet formulation which alleviates the disadvantages of mixing associated with the powder form.

SUMMARY OF THE INVENTION

It is therefore an object of the invention to provide an effervescent tablet dosage for inhibiting an ethylene response in plants comprising an agent for blocking the ethylene binding site in plants and an effervescent ingredient, in admixture with one or more acceptable carriers and/or excipients.

It is another object of the invention to provide a process for preparing the novel tablet dosage of the present invention.

It is a further object of the invention to provide a method for inhibiting the ethylene response in a plant.

DETAILED DESCRIPTION OF THE INVENTION

This invention provides a novel tablet dosage formulation containing an agent for blocking the ethylene binding site in plants and an effervescent ingredient, in admixture with one or more acceptable carriers and/or excipients.

According to the present invention, the agent for blocking the ethylene binding site in plants includes all the conventional compounds that inhibit ethylene responses in plants, such as, but not limited to, cyclopropene, 1-methylcyclopropene, 3,3-dimethycyclopropene, methylenecyclopropane, diazocyclopentadiene, trans-cyclooctene, cis-cyclooctene, and 2,5-norbornadiene. The relevant prior art, such as U.S. Pat. Nos. 3,879,188, 5,100,462, 5,518,988, and 6,017,849, and Sisler et al., Plant Growth Reg. 9, 157–164, 1990 are incorporated into the specification by reference in their entirety. Preferably, the agent for blocking the ethylene binding site in plants is 1-methylcyclopropene.

According to the present invention, the term "plant" is intended to include woody-stemmed plants in addition to field crops, potted plants, cut flowers, harvested fruits, vegetables and ornamentals.

Plants treated by the tablet dosage of the present invention that inhibit the ethylene response need to be treated with a non-phytotoxic amount. This phytotoxic level varies not only by plant but also by cultivar.

According to the present invention, numerous ethylene responses may be prevented, such as those disclosed in U.S. Pat. Nos. 5,518,988 and 3,879,188. Ethylene responses may be initiated by either exogenous or endogenous sources of ethylene. Ethylene responses include, for example, the ripening and/or senescence, of flowers, fruits and vegetables; the abscission of foliage, flowers and fruit; the ripening and/or shortening of the life of ornamentals, such as potted plants, cut flowers, shrubbery and dormant seedlings; the inhibition of growth in some plants such as the pea plant; and the stimulation of plant growth in some plants such as the rice plant.

According to the present invention, vegetables which may be treated to inhibit senescence include leafy green vegetables such as lettuce (e.g., *Lactuea sativa*), spinach (*Spinaca oleracea*) and cabbage (*Brassica oleracea*; various roots such as potatoes (*Solanum tuberosum*), carrots (*Daucus*); bulbs such as onions (*Allium* sp.); herbs such as basil (*Ocimum basilicum*), oregano (*Origanum vulgare*) and dill (*Anethum graveolens*); as well as soybean (*Glycine max*), lima beans (*Phaseolus limensis*), peas (*Lathyrus* sp.), corn (*Zea mays*), broccoli (*Brassica oleracea italica*), cauliflower (*Brassica oleracea botrytis*) and asparagus (*Asparagus Officinalis*).

According to the present invention, fruits which may be treated to inhibit ripening include tomatoes (*Lycopersicon esculentum*), apples (*Malus domes tica*), bananas (*Musa sapientum*), pears (*Pyrus communis*), papaya (*Carica papya*), mangoes (*Mangifera indica*), peaches (*Prunus persica*), apricots (*Prunus armeniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*), kiwi (*Actinidia Chinenus*), melons such as cantaloupes (*C. cantalupensis*) and musk melons (*C. melo*), pineapples (*Aranae comosus*), persimmon (*Diospyros* sp.) and raspberries (e.g., *Fragaria* or *Rubus ursinus*), blueberries (*Vaccinium* sp.), green beans (*Phaseolus vulgaris*), members of the genus *Cucumis* such as cucumber (*C. sativus*) and avocados (*Persea Americana*).

According to the present invention, ornamental plants which may be treated to inhibit senescence and/or to prolong flower life and appearance (such as the delay of wilting), include potted ornamentals and cut flowers. Potted ornamentals and cut flowers which may be treated with the methods of the present invention include azalea (*Rhododendron* spp.), hydrangea (*Macrophylla hydrangea*), hibiscus (*Hibiscus rosasanensis*), snapdragons (*Antirrhinum* sp.), poinsettia (*Euphorbia pulcherima*), cactus (e.g., *Cactaceae schlumbergera truncata*), begonias (*Begonia* sp.), roses (*Rosa* sp.), tulips (*Tulipa* sp.), daffodils (*Narcissus* sp.), petunias (*Petunia Hybrida*), carnation (*Dianthus caryophyllus*), lily (e.g., *Lilium* sp.), gladiolus (*Gladiolus* sp.), *Alstroemeria* (*Alstroemaria brasiliensis*), anemone (e.g., *Anemone bland*), columbine (*Aquilegia* sp.), aralia (e.g., *Aralia chinesis*), aster (e.g., *Aster carolinianus*), bougainvillea (*Bougainvillea* sp.), camellia (*Camellia* sp.), bellflower (*Campanula* sp.), cockscomb (*Celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

According to the present invention, plants which may be treated to inhibit abscission of foliage, flowers and fruit include cotton (*Gossypium* Spp.), apples, pears, cherries (*Prunus avium*), pecans (*Carva illinoensis*), grapes (*Vitis vinifera*), olives (e.g., *Olea europaea*), coffee (*Cofffea arabica*), snapbeans (*Phaseolus vulgaris*), and weeping fig (*Ficus benjamina*), as well as dormant seedlings such as various fruit trees including apple, ornamental plants, shrubbery, and tree seedlings.

In addition, according to the present invention, shrubbery which may be treated to inhibit abscission of foliage include privet (*Ligustrum* sp.), photinea (*photina* sp.), holly (*Ilex* sp.), ferns of the family polypodiaceae, schefflera (*Schefflera* sp.), aglaonema. (*Aglaonema* sp.), cotoneaster (*Cotoneaster* sp.), barberry (*Berberris* sp.), waxmyrtle (*Myrica* sp.), abelia (*Abelia* sp.), acacia (*Acacia* sp.), and bromeliades of the family Bromeliaceae.

According to the present invention, the effervescent ingredient is to control the speed of dissolution of the agent for blocking the ethylene binding site in plants in aqueous solution. Any reaction mixture which may generate an effervescent effect may be used in the present invention. The preferred embodiment of the effervescent ingredient of the present invention comprises a mild alkaline compound and a mild acid compound, which is in solid form at normal temperature. The mild alkaline compound with the mild acid compound, in the presence of a solvent, to generate of carbon dioxide gas.

According to the present invention, the ratio of the mild alkaline compound to the mild acid compound is from about 9:1 to about 1:1. Preferably, the ratio is about 4:1.

The preferred embodiment of the mild acid compound is tartaric acid, citric acid, fumaric acid, salicylic acid, oxalic acid, succinic acid, maleie acid malic acid, glycolic acid, omithuric acid, and gluconic acid, and more preferably malic acid.

According to the present invention, the amount of the agent for blocking the ethylene binding site in plants is from about 0.01% to about 0.5%. Preferably, the amount is from about 0.05% to about 0.24%.

All carriers or excipients which have been conventionally used in the field of preparing tablet dosage formulations are suitable for use in the present invention. The preferred embodiments of the carriers and excipients include, but are not limited to, glyceryl/polyethylene glycol behenate.

The major advantage of the dosage of the subject invention is that it provides an effective, truly user-friendly dosage form suitable for non-technical customers, florists, and wholesalers. The effervescent tablet dosage alleviates the disadvantages of mixing associated with the power form.

The present invention further provides a process for preparing the tablet dosage of the subject invention. Persons skilled in the art of preparing tablet dosage formulations may adopt all the conventional processes to practice the tablet dosage of the present invention.

According to the present invention, the conventional processes for preparing the claimed tablet dosage include mixing the ingredients and passing the mixed powder into a die, and then compressing the die in a pressure between about 5 to about 8 $kg/cm^2$ into a dosage.

The tablet dosage of the present invention can be made into appropriate doses for easy handling. For good protection during storage and transportation, the tablets of the present may be packaged at a low passing the mixed powder into a die, and then compressing the die in a pressure between about 5 to about 8 $kg/cm^2$ into a dosage.

The tablet dosage of the present invention can be made into appropriate doses for easy handling. For good proton during storage and transportation, the tablets of the present may be packaged at a low relative humidity, such as less th 30%, in blister-plastic pack, or may be enclosed in aluminum foil.

Another embodiment of the present invention is a method for inhibiting an ethylene response in a plant. The method comprises contacting the effervescent tablet dosage of the subject invention with a solvent. The agent for blocking the ethylene binding site in plants is liberated from the tablet dosage through an effervescent action to the air, and contacts with the plants.

The effervescent action of the present invention facilitates the bursting of the tablet in an aqueous solvent, thereby promoting the release of the blocking agent to the treated space environment. Additionally, convective force of the gas in the effervescent action in an aqueous solvent provides the mixing needed for the uniform dissolution and the release of the blocking agent to the environment.

According to the present invention, the solvents used herein include, but are not limited to, water aid a dilute alkaline solution.

Without further elaboration, it is believed that one skilled in the art can, based on the above disclosure and the examples described below, utilize the present invention to its fullest extent. The following examples are to be construed as merely illustrative examples of how one skilled in the art can practice the claimed methods and are not limitative of the remainder of the disclosure in any way.

EXAMPLE 1

The Preparation for the Tablet Dosage

The following general procedures can be used to prepare tablet dosages. Generally, the steps are conducted in a controlled environment having a low relative humidity, such as less than 30%, and temperature at 25° C. All ingredients are thoroughly mixed. Then, using a tablet press equipped with a mold of given size and shape, the powder blend is subjected to compression pressured at about 8 kg/cm². The tablets are then inspected and stored at a low relative humidity for subsequent packaging in blister-plastic pack aluminum foil.

EXAMPLE 2

Comparison Tests

A. Non-Effervescent Methylcyclopropene Tablets

A 10 g 1-methylcyclopropene powder (AnsiP® from Lytone Enterprise, Inc. Taipei Taiwan, ROC) was formulated into tablet form according to the process given in the above example. The tablet form contains 0.5 to 1 g of 1-methylcyclopropene powder per tablet. A small amount of lubricant was needed to prevent the tablet form adhering to the mold. Two fords of tablets were made in the test. One form contained an additional bulking agent and the other form did not contain the bulking agent. The resulting tablets were tested for solubility by dropping them into water or a dilute alkaline solution. It was observed that the bursting action and dissolution of tablets was very slow, even with the tablet containing the bulking agent. After 4 hours, they were still not completely dispersed or dissolved. Therefore, it was deemed unsatisfactory to make 1-methylcyclopropene powder into a tablet form without an effervescent action.

B. Effervescent 1-methylcyclopropene Tablets

1-Methylcyclopropene powder was formulated into effervescent tablets containing 40% in weight of $NaHCO_3$, 10% of malic acid, and 50% of 1-methylcyclopropene powder by the preparation process given above. Each tablet weighs from 0.5 to 2 g depending on the size of the mold used. The effervescent tablets immediately fizzed when dropped into water and completely dissolved into the water in less than 60 minutes.

EXAMPLE 3

The Formulations of the Tablet Dosage

The tablet dosage of the present invention may be formulated as the following:

| Formulation A | |
|---|---|
| Ingredient | Amount per Tablet |
| 1-Methylcyclopropene powder (containing 0.1 to 0.5% 1-methylcyclopropene with the balance being inert carrier) | 500 mg |
| $NaHCO_3$ | 400 mg |

| Formulation A (continued) | |
|---|---|
| Ingredient | Amount per Tablet |
| Malic acid | 100 mg |
| Glyceryl/polyethylene glycol behenate | 50 mg |

What is claimed is:

1. An effervescent tablet dosage comprising an agent for blocking the ethylene binding site in plants and an effervescent ingredient, in admixture with one or more acceptable carriers and/or excipients.

2. The tablet dosage of claim 1, wherein the agent for blocking the ethylene binding site in plants is selected from the group consisting of cyclopropene, 1-methylcyclopropene, 3,3-dimethycyclopropene, methylenecyclopropane, diazocyclopentadiene, trans-cyclooctene, cis-cyclooctene, and 2,5-norbornadiene, the derivatives thereof, and the mixtures thereof.

3. The tablet dosage of claim 2, wherein the agent for blocking the ethylene binding site in plants is 1-methylcyclopropene.

4. The tablet dosage of claim 1, wherein the effervescent ingredient comprises a mild alkaline compound and a mild acid compound which is in a solid state at normal temperature.

5. The tablet dosage of claim 4, wherein the mild alkaline compound is selected from the group consisting of $NaHCO_3$, $KHCO_3$, $CaCO_3$, $Na_2CO_3$, $K_2CO_3$, $NaKCO_3$, sodium glycine carbonate and the mixtures thereof.

6. The tablet dosage of claim 4, wherein the mild acid compound is selected from the group consisting of tartaric acid, citric acid, fumaric acid, salicyclic acid, oxalic acid, succinic acid, malic acid, maleic acid, glycolic acid, ornithuric acid, gluconic acid and the mixtures thereof.

7. The tablet dosage of claim 1, wherein the amount of the agent for blocking the ethylene binding site in plants is from about 0.01% to about 0.5%.

8. The tablet dosage of claim 7, wherein the amount of the agent for blocking the ethylene binding site in plants is from about 0.05% to about 0.24%.

9. The tablet dosage of claim 4, wherein the ratio of the mild alkaline compound to the mild acid compound is from about 9:1 to about 1:1.

10. The tablet dosage of claim 9, wherein the ratio of the mild alkaline compound to the mild acid compound is about 4:1.

11. The tablet dosage of any one of claim 1, wherein the agent for blocking the ethylene binding site in plants is released in a gaseous form.

12. A process of preparing the tablet dosage of claim 1 comprising (i) mixing an agent for blocking the ethylene binding site in plants, an effervescent ingredient, and one or more acceptable carriers and/or excipients, (ii) passing the mixture into a dies; and (iii) compressing the die into a dosage.

13. A method for inhibiting an ethylene response in a plant, comprising (i) contacting the effervescent tablet dosage of claim 1 with a solvent, thereby liberating the agent for blocking the ethylene binding site in the plant from the tablet dosage through an effervescent action; and (iii) contacting the agent with the plant.

14. The method of claim 13, wherein the solvent is selected from water and a dilute alkaline solution.

15. The method of claim 14, wherein the solvent is water.

* * * * *

Disclaimer

6,897,185 B1 - William T. H. Chang, Taipei (TW); Ren-Der Yang, Shrewsbury, MA (US). FORMULATION FOR COUNTERACTING AND ETHYLENE RESPONSE IN PLANTS, PREPARATION PROCESS THEREOF, AND METHOD USING THE SAME. Patent dated May 24, 2005. Disclaimer filed April 28, 2021, by the inventors.

I hereby disclaim the following complete claims 1-2, 4-10 and 12-15 of said patent.

*(Official Gazette, September 13, 2022)*